United States Patent [19]

Williams, III

[11] 3,989,712
[45] Nov. 2, 1976

[54] THIO-BIS(PHTHALIMIDES)

[75] Inventor: Frank J. Williams, III, Scotia, N.Y.

[73] Assignee: General Electric Company, Schenectady, N.Y.

[22] Filed: Mar. 30, 1973

[21] Appl. No.: 346,470

[52] U.S. Cl............................ 260/326 S; 260/346.3
[51] Int. Cl.$^2$......................................... C07D 209/38
[58] Field of Search....................... 260/346.3, 326 S

[56] References Cited
UNITED STATES PATENTS

| | | | |
|---|---|---|---|
| 3,374,274 | 3/1968 | Spainhour | 260/609 E |
| 3,422,064 | 1/1969 | Gall | 260/65 |
| 3,692,740 | 9/1972 | Suzuki et al. | 260/65 |

FOREIGN PATENTS OR APPLICATIONS 2,155,431  8/1972  Germany

OTHER PUBLICATIONS

Zakoshchikov et al., Vysokomol. Soedin, Ser. A1969, 11(11), 2487–2492, Chem. Abstracts, 1970, vol. 72, 67438.

Primary Examiner—Henry R. Jiles
Assistant Examiner—Bernard Dentz
Attorney, Agent, or Firm—William A. Teoli; Joseph T. Cohen; Jerome C. Squillaro

[57] ABSTRACT

A method is provided for making bis(thioetherphthalic anhydride)s from bis(thioetherphthalimide)s. The latter compounds can be made by using an alkali metal sulfide with an N-substituted phthalimide having an alkali metal sulfide displaceable radical attached to the ring.

3 Claims, No Drawings

THIO-BIS(PHTHALIMIDES)

The present invention relates to a method for converting N-substituted phthalimides to bis(thioetherphtalimide)s and bis(thioetherphthalic anhydride)s and to the products made thereby.

Included among the compounds provided by the present invention are bis(thioetherphthalic anhydride)s of the formula

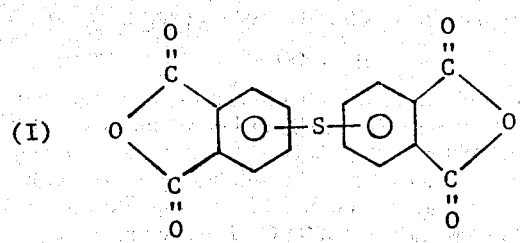

These compounds can be employed as anti-oxidants in various organic materials such as rubber, hydrocarbon oils, polypropylene, etc.; curing agents for epoxy resins; intermediates for polyester resins, etc.

There also is provided by the present invention, a method for making the compounds of formula I which comprises, 1. effecting reaction between an alkali metal sulfide $M_2S$, and an N-substituted phthalimide of the formula

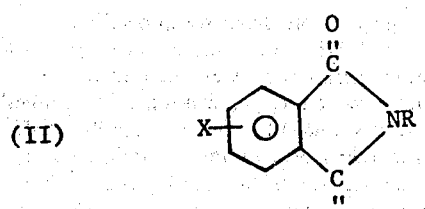

to produce an intermediate N-substituted bis(thioetherphthalimide) of the formula,

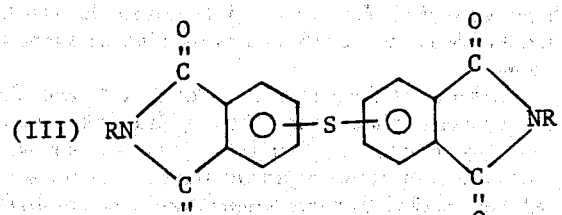

2. hydrolyzing the bis(thioetherphthalimide) in the presence of base to produce the corresponding bis(thioetherphthalic acid salt), 3. acidifying the bis(thioetherphthalic acid salt) and recovering the resulting bis(thioetherphthalic acid), and 4. dehydrating the bis(thioetherphthalic acid) to the corresponding bis(thioetherphthalic anhydride), where X is a radical selected from fluoro, chloro, bromo, iodo and nitro, R is a monovalent radical selected from $C_{(1-8)}$ alkyl radicals, and $C_{(6-20)}$ aromatic radicals, and M is an alkali metal such as sodium, potassium and lithium.

Radicals included by R are, for example, methyl, ethyl, propyl, butyl, pentyl, etc; phenyl, tolyl, xyyl, naphthyl, chlorophenyl, bromotolyl, etc.

Included by the bis(thioetherphthalic anhydride)s of formula I are, for example, bis(2,3-dicarboxyphenyl)-sulfide dianhydride, bis(3,4-dicarboxyphenyl)sulfide dianhydride, 2,3-dicarboxyphenyl-3',4'-dicarboxyphenylsulfide dianhydride, etc.

Some of the N-substituted bis(thioetherphthalimide)s of formula III are, for example, 3,3'-bis(N-phenylphthalimide)sulfide, 4,4'-bis(N-phenylphthalimide)sulfide, 3,3'-bis(N-butylphthalimide)sulfide, 4,4'-bis(N-butylphthalimide)sulfide, 3,3'-bis(N-methylphthalimide)sulfide, 4,4'-bis(N-methylphthalimide)sulfide, 3,4'-bis(N-phenylphthalimide)sulfide, etc. These bisimide sulfides can be employed as plasticizers, fire retardants, anti-oxidants in organic polymers such as polyvinylchlorides, polyimides, aromatic hydrocarbon greases.

The N-substituted phthalimides of formula II can be made by effecting reaction between substantially equal moles of organic amine $RNH_2$, where R is as previously defined, and a substituted phthalic anhydride of the formula,

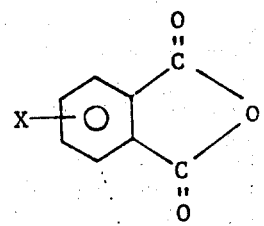

where X has been previously defined. Included by $RNH_2$ are organic amines such as aniline, toluidine, etc., methylamine, ethylamine, etc.

The alkali sulfide, for example, sodium sulfide which can be employed can be utilized in the hydrated form ($Na_2S \cdot 9 H_2O$) or in anhydrous form by azeotroping the water of hydration from the salt, removing the water of hydration by heating the salt at temperatures up to about 400° C under vacuum, or using commercial anhydrous sodium sulfide.

In the practice of the invention, reaction is effected between the N-substituted phthalimide, or "phthalimide" of formula II, and the alkali sulfide to produce the N-substituted bis(phthalimide)sulfide or "bisimide sulfide" of formula III. The bisimide sulfide is thereafter hydrolyzed to the bis(phthalic acid) sulfide salt or "tetra-acid" salt which is acidified to produce the tetra-acid. Dehydration of the tetra-acid results in the production of the bis(thioetherphthalic anhydride) or "bis anhydride sulfide" of formula I.

Reaction between the phthalimide and the alkali sulfide to produce the bisimide can be effected at 25° C to 150° C in the presence of a dipolar aprotic organic solvent such as dimethylformamide, dimethylsulfoxide, hexamethylphosphoric triamide, dimethylacetamide, etc. Mixtures of such solvents, with non-polar solvents such as toluene, chlorobenzene, dichlorobenzene, etc. also can be employed. In addition, phosphonium salts can be used in combination with non-polar solvents. Reaction time can vary between 5 minutes to 16 hours or more, depending upon temperature, degree of agitation, etc.

Recovery of the bisimide from the resulting mixture can be achieved by filtering the mixture and treating the filtrate with an aqueous acidic mixture such as dilute hydrochloric acid.

Hydrolysis of the bisimide to the tetra-acid salt can be effected by contacting the bisimide to a refluxing aqueous base solution, such as a 10 to 50% solution of an alkali hydroxide, for example, sodium hydroxide. Other bases which can be employed are potassium hydroxide, magnesium hydroxide, etc. Hydrolysis of the bisimide can be effected within 1 to 48 hours or more, depending upon reactants, degree of agitation, temperature, etc. Organic amine by-product can be removed by standard procedures such as steam distillation, etc. In addition, the rate of hydrolysis is greatly accelerated by carrying out the reaction above atmospheric pressure at temperatures in the range of from 150° C to 200° C.

The bisimide hydrolysis product can then be acidified with a mineral acid, such as dilute hydrochloric. The resulting tetra-acid can thereafter be dehydrated at temperatures in the range of 100° C to 200° C using a dehydrating agent such as acetic anhydride, acetyl chloride, dicyclohexylcarbodiimide (DCC), etc. Recovery and purification of final product can be achieved by standard technique.

In order that those skilled in the art will be better able to practice the invention, the following examples are given by way of illustration and not by way of limitation. All parts are by weight.

EXAMPLE 1

A mixture of 1 part anhydrous sodium sulfide, 6.85 parts 3-nitro-N-phenylphthalimide and about 66 parts of DMF was stirred at room temperature under a nitrogen atmosphere for 1 hour. The solution was heated at 70° C for 2 hours and cooled to room temperature. The solution was filtered, the filtrate was added to acidic water and the resulting precipitate was collected and dried to give 5.3 parts (95% yield) of 3,3'-bis(N-phenylphthalimide)sulfide. Recrystallization from toluene gave a sample m.p. 248°–250° C. The identity of the product was confirmed by its Ir, nmr, and mass spectra analysis as well as by its $^{13}C$ spectra.

A blend is made of about two parts of the above bisimide sulfide with about 100 parts of an aromatic hydrocarbon lubricating grease. The grease is found to have improved anti-oxidant properties.

EXAMPLE 2

A mixture of 1 part of anhydrous sodium sulfide, 6.85 parts of 4-nitro-N-phenylphthalimide and about 66 parts of DMF was heated at 70° C under a nitrogen atmosphere for 4½ hours. The solution was cooled to room temperature and the resulting precipitate was collected, washed with DMF and water and dried to give 3.5 parts of 4,4'-bis-(N-phenylphthalimide)sulfide (56% yield). Recrystallization from ortho-dichlorobenzene gave a sample m.p. 293°–295° C. The identity of the product was established by its Ir, nmr, and mass spectra analysis as well as by its $^{13}C$ spectra.

EXAMPLE 3

A mixture of 1 part anhydrous sodium sulfide, 6.6 parts of 3-chloro-N-phenylphthalimide and about 40 parts of DMF was stirred at 100° C. for 16 hours under a nitrogen atmosphere. The solution was cooled to room temperature and filtered and the filtrate was added to 500 parts of 1.2 NHCl. The resulting precipitate was filtered and dried to give 5.7 parts (90% yield) of 3,3-bis(N-phenylphthalimide)sulfide identical to the product from Example 1.

EXAMPLE 4

A mixture of 1 part anhydrous sodium sulfide, 6.6 parts of 4-chloro-N-phenylphthalimide and about 50 parts of DMF was stirred at 100° C for 16 hours under a nitrogen atmosphere. The solution was cooled to room temperature and the resulting precipitate was collected by filtration, washed with DMF, and dried to give 6.2 parts (95% yield) of 4,4'-bis(N-phenylphthalimide)sulfide identical to the product from Example 2.

EXAMPLE 5

A mixture of 1 part of anhydrous sodium sulfide, 6.35 parts 3-nitro-N-butylphthalimide and about 90 parts of anhydrous dimethylformamide were heated at 70° C under a nitrogen atmosphere for 2 hours. The cooled reaction mixture was added to 500 parts of 1.2 NHCl and the resulting yellow precipitate was collected and dried. In this manner 4.7 parts (85% yield) of 3,3'-bis(N-butylphthalimide)sulfide was collected, m.p. 123°–125° C. The product was identified from its infrared and carbon and proton nmr spectra.

EXAMPLE 6

A mixture of 1 part 3,3'-bis(N-phenylphthalimide)sulfide of Example 1, and 1 part 50% aqueous sodium hydroxide solution was stirred at 176° C for 3 hours. The solution was cooled and extracted well with ether. The aqueous layer was added to 20 parts of acidic water and the resulting precipitate was collected and dried to give 0.53 parts of bis(2,3-dicarboxyphenyl)sulfide. Its identity was confirmed by its infrared and nmr spectra.

A mixture of 0.53 part of the above crude acid, 25 parts glacial acetic acid and about 1 part acetic anhydride was refluxed for four hours. The solution was concentrated by removing about 20 parts of acetic acid and then cooled to room temperature. The resulting precipitate was collected and dried to give 0.5 parts (75% yield based on bisimide) of a yellow powder m.p. 240°–242° C. Based on method of preparation, its infrared, nmr and mass spectra, the product was bis(2,3-dicarboxyphenyl)sulfide dianhydride.

Ten parts of the above bis sulfide dianhydride is blended with 100 parts of a liquid epoxy Novolak resin having an epoxy equivalent weight of about 178. It is found that the blend cures to a solid at ambient temperatures after several hours.

EXAMPLE 7

A mixture of 1 part 4,4-thiobis-N-phenylphthalimide and 1 part 50% aqueous sodium hydroxide solution was stirred at 176° C (135 psi) for 3½ hours. The solution was cooled and extracted well with ether. The aqueous solution was added to 20 parts of acidic water and the resulting precipitate was dried to give 0.54 parts of bis(3,4-dicarboxyphenyl)sulfide. Its identity was confirmed by its infrared and nmr spectra.

A mixture of 0.54 part of the above crude acid, 35 parts glacial acetic acid and about 1 part acetic anhydride was refluxed for 4 hours. The solution was concentrated by removing about 30 parts of acetic acid and then cooled to room temperature. The resulting precipitate was collected and dried to give 0.5 parts (75% yield based on bisimide) of a white powder, m.p. 202°–203° C. Based on method of preparation, its infrared, nmr and mass spectra, the product was bis(3,4-dicarboxyphenyl)sulfide dianhydride.

EXAMPLE 8

A mixture of 1 part 3,3-thiobis-N-phenylphthalimide, 25 parts of 50% aqueous sodium hydroxide solution and 25 parts distilled water was heated at reflux for 6 hours. The solution was cooled to room temperature, extracted with ether and the aqueous layer acidified. The acidic aqueous layer was extracted well with ether, the ether extracts washed with a saturated salt solution and dried over anhydrous magnesium sulfate. Removal of the drying agent and concentration of the solution gave a tan solid whose infrared spectra was identical to that of the acid obtained in Example 6.

The crude acid was dehydrated by refluxing with acetic anhydride, acetic acid as described in Example 6 to give a tan solid. Recrystallization from toluene gave a sample m.p. 231°–234° C whose infrared, nmr and mass spectra were identical to those of bis(2,3-dicarboxyphenyl)sulfide dianhydride obtained in Example 6.

It should be understood that the above examples represent only a limited number of bisimide sulfides and bis sulfide anhydrides which can be made in accordance with the practice of the invention which are shown respectively by formulas III and I.

What I claim as new and desire to secure by Letters patent of the United States is:
1. 3,3′-bis(N-phenylphthalimide)sulfide.
2. 4,4′-bis(N-phenylphthalimide)sulfide.
3. 3,3′bis(N-butylphthalimide)sulfide.

* * * * *